(12) United States Patent
Burk et al.

(10) Patent No.: US 6,376,533 B1
(45) Date of Patent: Apr. 23, 2002

(54) OMEGA-CYCLOALKYL 17-HETEROARYL PROSTAGLANDIN E2 ANALOGS AS EP2-RECEPTOR AGONISTS

(75) Inventors: Robert M. Burk, Laguna Beach; Mark Holoboski; Mari F. Posner, both of Laguna Niguel, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/693,722

(22) Filed: Oct. 20, 2000

(51) Int. Cl.$^7$ .................. A61K 31/38; A61K 31/41; C07D 333/16; C07D 257/00
(52) U.S. Cl. .................. 514/438; 514/381; 549/78; 549/79; 548/252
(58) Field of Search ............. 549/78, 79; 514/438, 514/381; 548/252

(56) References Cited

U.S. PATENT DOCUMENTS

| | | | | |
|---|---|---|---|---|
| 4,275,224 A | * | 6/1981 | Kluender et al. | 560/116 |
| 4,994,274 A | | 2/1991 | Chan et al. | |
| 5,028,624 A | | 7/1991 | Chan et al. | |
| 5,034,413 A | | 7/1991 | Chan et al. | |
| 5,446,041 A | | 8/1995 | Chan et al. | |
| 5,578,618 A | * | 11/1996 | Stjernschantz et al. | 514/365 |
| 6,107,338 A | * | 8/2000 | Wos et al. | 514/530 |
| 6,262,293 B1 | * | 7/2001 | Tani et al. | 560/18 |
| 6,265,440 B1 | * | 7/2001 | Ueno et al. | 514/530 |
| 6,265,444 B1 | * | 7/2001 | Bowman et al. | 514/570 |
| 6,288,113 B1 | * | 9/2001 | Egi et al. | 514/530 |

OTHER PUBLICATIONS

Bito, L.Z., *Biological Protection with Prostaglandins*, "Prostaglandins and Related Compounds as Potential Ocular Therapeutic Agents", vol. 1, Chapter 18, 1985, pp. 231–252.
Bito, L.Z., *Glaucoma, Applied Pharamacology in the Medical Treatment*, "Prostaglandins, Other Eicosanoids, and Their Derivatives as Potential Antiglaucoma Agents", 1984, Chapter 20, pp. 477–505.
Nilsson et al, Invest. Ophthalmol. Vis. Sci. (suppl), 284 (1987), Arvo Abstracts 9–6:00.
Bito, L.Z., Arch. Ophthalmol. "Prostaglandins" "Old Concepts and New Perspectives", vol. 105, pp. 1036–1039 (1987).
Siebold et al, Prodrug 5 3, "Esterified protaglandin shows 'potent' promise", 1989.

* cited by examiner

*Primary Examiner*—Deborah C. Lambkin
(74) *Attorney, Agent, or Firm*—Robert J. Baran; Martin A. Voet; Carlos A. Fisher (57) ABSTRACT

The invention relates to the use of derivatives of E-type prostaglandins as $EP_2$ agonists, in general, and, in particular as ocular hypotensives. The PGE derivatives used in accordance with the invention are represented by the following formula I:

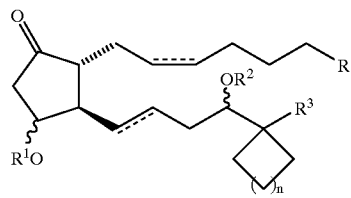

wherein the hatched segment represents an α bonds, the solid triangle represents a β bond, the wavy segments represent α or β bond, dashed lines represent a double bond or a single bond, $R^3$ is heteroaryl or a substituted heteroaryl radical, $R^1$ and $R^2$ are independently selected from the group consisting of hydrogen or a lower alkyl radical having up to six carbon atoms, or a lower acyl radical having up to six carbon atoms, R is selected from the group consisting of $CO_2R^4$, $CONR^4{}_2$, $CH_2OR^4$, $CONR^4SO_2R^4$, $P(O)(OR^4)$ and

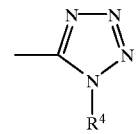

wherein $R^4$ is selected from the group consisting of H, phenyl and lower alkyl having from one to six carbon atoms and n is 0 or an integer of from 1 to 4.

27 Claims, 2 Drawing Sheets

OMEGA-CYCLOALKYL 17-HETEROARYL PROSTAGLANDIN E2 ANALOGS AS EP2-RECEPTOR AGONISTS

BACKGROUND OF THE INVENTION

1. Field of the Invention

The present invention relates to ω-cycloalkyl 17-heteroaryl prostaglandin $E_2$ analogs as $EP_2$-receptor agonists. These compounds are potent ocular hypotensive and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ (PGEI), prostaglandin $E_2$ (PGE$_2$)], and on the configuration of the substituents on the alicyclic ring indicated by α or β [[e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), now U.S. Pat. No. 5,446,041, relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed Dec. 29, 1993). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed Jul. 7, 1989, now U.S. Pat. No. 4,994,274), Ser. No.

584,370 (filed Sep. 18, 1990, now U.S. Pat. No. 5,028,624) and Ser. No. 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I wherein the hatched segment represents an α bond, the solid triangle represents a β bond, the wavy segment represents α or β bond, dashed lines represent a double bond or a single bond, $R^3$ is heteroaryl or a substituted heteroaryl radical, $R^1$ and $R^2$ are independently selected from the group consisting of hydrogen or a lower alkyl radical having up to six carbon atoms, or a lower acyl radical having up to six carbon atoms, R is selected from the group consisting of $CO_2R^4$, $CONR^4{}_2$, $CH_2OR^4$, $CONR^4SO_2R^4$, $P(O)(OR^4)$ and wherein $R^4$ is selected from the group consisting of H, phenyl and lower alkyl having from one to six carbon atoms and n is 0 or an integer of from 1 to 4.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application. In particular, the substituents on the heteroaryl radical may be selected from the group consisting of lower alkyl, e.g. $C_1$ to $C_6$ alkyl; $OR^4$; $CO_2R^4$; halogen, e.g. fluoro, chloro and bromo; trifluoromethyl ($CF_3$); $COR^4$, e.g. $COCH_3$; $COCF_3$; $SO_2NR^4$, e.g. $SO_2NH_2$; $NO_2$; CN; etc.

In a still further aspect, the present invention relates to a pharmaceutical product, comprising a container adapted to dispense its contents in a metered form; and an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of ω-cycloalkyl 17-heteroaryl prostaglandin $E_2$ analogs as $EP_2$-receptor agonists. The compounds used in accordance with the present invention are encompassed by the following structural formula I:

wherein the substituents and symbols are as hereinabove defined. The dotted lines on bonds between carbons 5 and 6 (C-5) and carbons 13 and 14 (C-13) indicate a single or double bond. If two solid lines are used at C-5, or C-13, it indicates a specific configuration for that double bond. Hatched lines used at position C-8, C-9 and C-11 indicate the α configuration. A triangle at position C-12 represents β orientation.

A preferred group of the compounds of the present invention includes compounds that have the following structural formula II:

wherein Z is selected from the group consisting of O and S, A is selected from the group consisting of N, —CH, and C, $R^5$ is selected from the group consisting of hydrogen, halogen, lower alkyl having from 1 to 6 carbon atoms and lower alkoxy having from 1 to 6 carbon atoms, $R^6$ and $R^7$ are selected from the group consisting of hydrogen, halogen, lower alkyl having from 1 to 6 carbon atoms and lower alkoxy having from 1 to 6 carbon atoms, or, together with $R^6$ and $R^7$ forms a condensed aryl ring.

Another preferred group includes compounds having the formula III:

In the above formulae, the substituents and symbols are as hereinabove defined.

The above compounds of the present invention may be prepared by methods that are known in the art or according to the working examples below. The compounds, below, are especially preferred representative of the compounds of the present invention.

- 7- {(1R,2R,3R)-3-Hydroxy-2-[(E)-4-hydroxy-4-(1-thiophen-2-yl-methylcyclobutyl)but-1-enyl]-5-oxocyclopentyl}heptanoic acid methyl ester
- 7- {(1R,2R,3R)-3-Hydroxy-2-[(E)-4-hydroxy-4-(1-thiophen-2-yl-methylcyclobutyl)but-1-enyl]-5-oxocyclopentyl}heptanoic acid
- (Z)-7-{(1R,2R,3R)-3-Hydroxy-2-[(E)-4-hydroxy-4-(1-thiophen-2-yl-methylcyclobutyl)but-1-enyl]-5-oxocyclopentyl}hept-5-enoic acid methyl ester
- (Z)-7- {(1R,2R,3R)-3-Hydroxy-2-[(E)-4-hydroxy-4-(1-thiophen-2-yl-methylcyclobutyl)but-1-enyl]-5-oxocyclopentyl}hept-5-enoic acid A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 1:
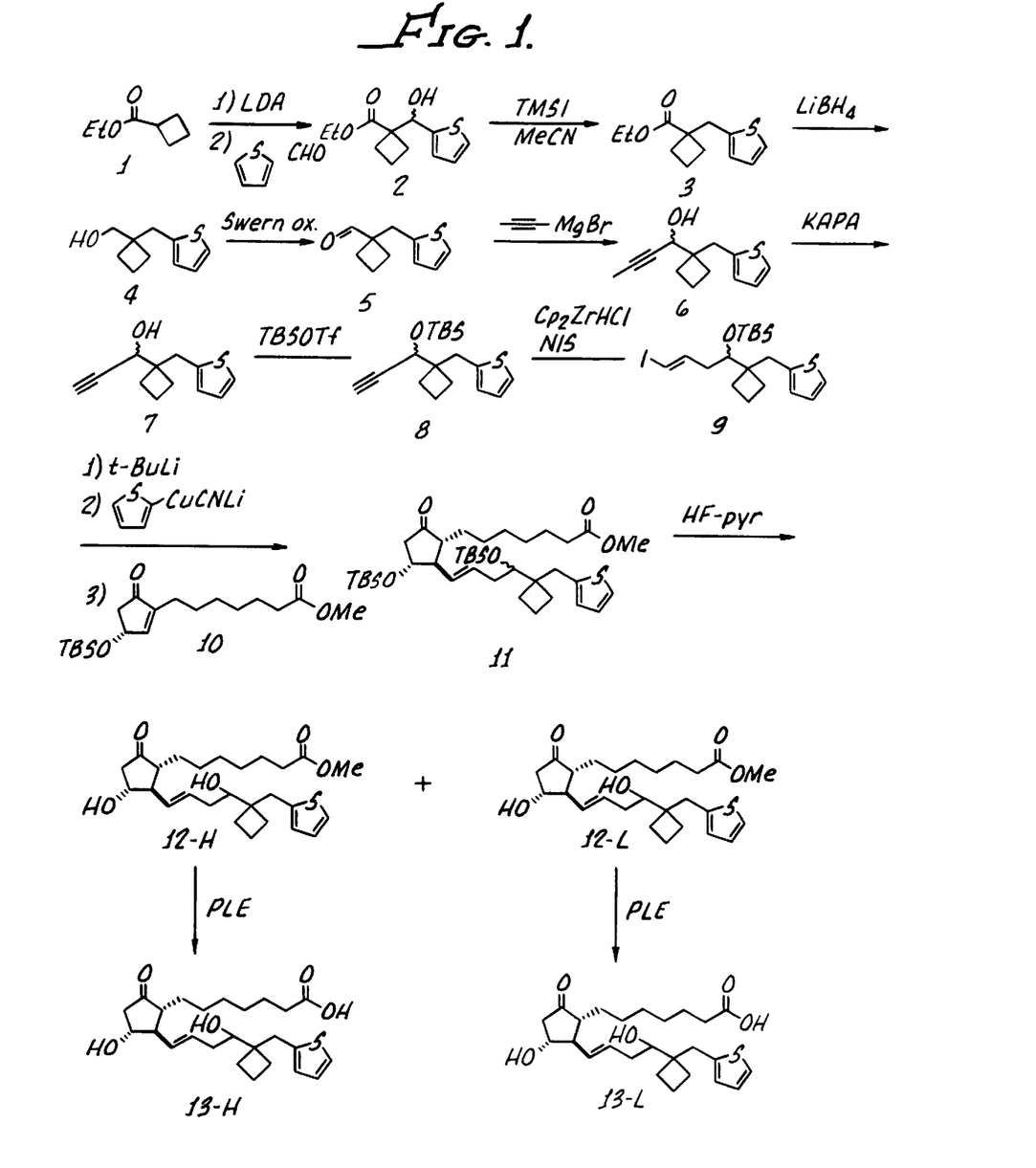
FIG. 1 is a schematic of the chemical synthesis of certain compounds of the invention specifically disclosed as Examples 12H and L and 13H and L.
Figure 2:
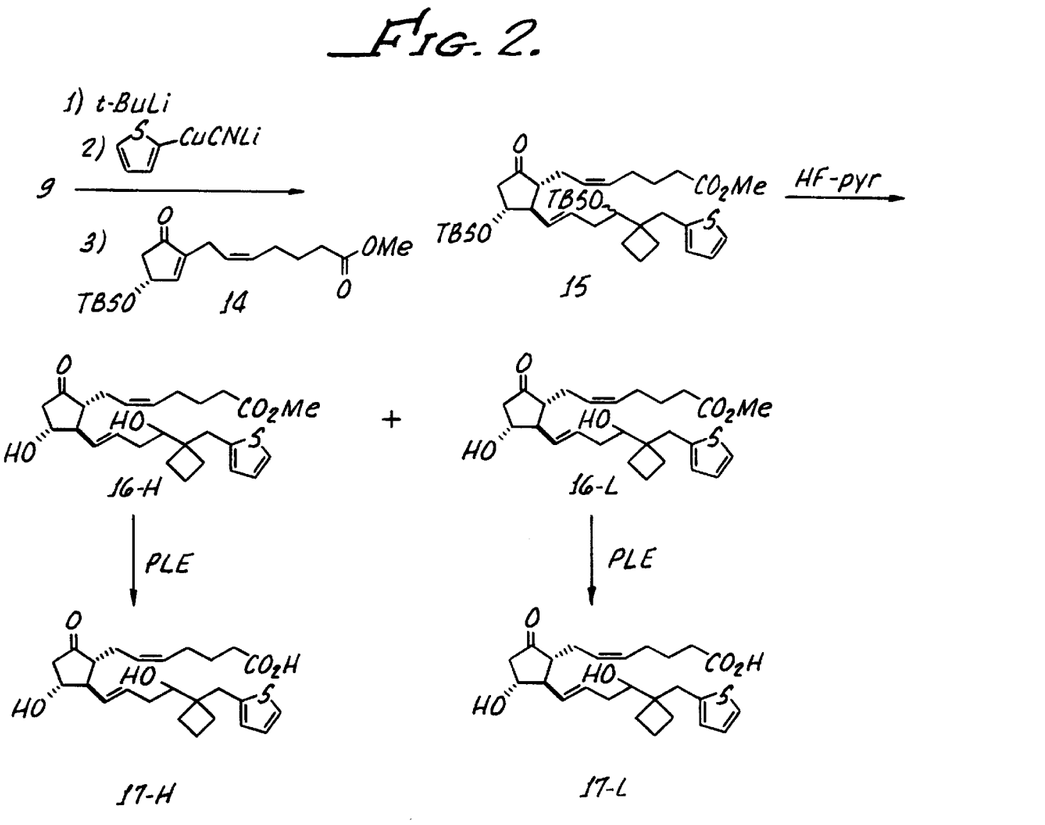
FIG. 2 is a schematic of the chemical synthesis of certain compounds of the invention specifically disclosed as Examples 16H and L and 17H and L.

The invention is further illustrated by the following non-limiting Examples, which are summarized in the reaction schemes of FIGS. 1 and 2, wherein the compounds are identified by the same designator in both the Examples and the Figures.

EXAMPLE 1

Ethyl Cyclobutanecarboxylate Acid Ethyl Ester (1)

The named compound was purchased from Aldrich Chemical Co., P.O. Box 2060, Milwaukee, Wis. 53201 USA.

EXAMPLE 2

1-(1-Hydroxy-1-thiophen-2-yl-methyl) cyclobutanecarboxylic Acid Ethyl Ester (2)

Lithium diisopropylamide mono(THF) (1.95 mL of a 2.0M solution in heptane/THF/ethylbenzene, 3.90 mmol) was added to a solution of ester 1 (0.50 g, 3.9 mmol) in THF (6 mL) at −78° C. After stirring 30 min, 2-thiophenecarboxaldehyde (667 mg, 5.95 mmol) was added and the mixture was stirred for 3 h. After the reaction was judged complete by TLC analysis, saturated aqueous $NH_4Cl$ was added and the reaction was slowly warmed to 23° C. The THF was evaporated and the reaction mixture was extracted with $CH_2Cl_2$ (2×). The combined organic layers were washed with brine, dried ($Na_2SO_4$), filtered and concentrated in vacuo. Purification of the residue by flash column chromatography (FCC) (silica gel, 100% hexane followed by 9:1 hexane/EtOAc) afforded the above named compound 2.

EXAMPLE 3

1-Thiophen-2-yl-methylcyclobutanecarboxylic Acid Ethyl Ester (3)

Trimethylsilyliodide (20 g, 100 mmol) was added to $CH_3CN$ (10 mL) at 0° C. and the mixture was allowed to stir 5 min. A solution of alcohol 2 (5 g, 20 mmol) in $CH_3CN$ (10 mL) was added slowly while the temperature was kept between 4–10° C., and the reaction was allowed to warm to 23° C. After stirring for 2 h at 23° C., the reaction was judged complete via TLC analysis. The mixture was poured into 3N NaOH at 0° C. and EtOAc was added. The organic layer was separated, washed with brine, dried ($Na_2SO_4$), filtered and concentrated in vacuo. FCC (silica gel, 1:1, hexane/$CH_2Cl_2$) gave 2.3 g of the above named ester 3.

EXAMPLE 4

(1-Thiophen-2-yl-methylcyclobutyl)methanol (4)

Lithium borohydride (435 mg, 20 mmol) was added to a solution of ester 3 (2.3 g, 10 mmol) in $Et_2O$ (20 mL) at 0° C. After having stirred for 5 min, MeOH (640 mg, 20 mmol) was added dropwise and stirring continued at 0° C. until effervescence ceased. The mixture was warmed to 23° C. and was allowed to stir an additional hour, at which time the mixture was poured into 3N NaOH and stirred an additional 0.5 h. The organic layer was separated and washed with brine, dried ($Na_2SO_4$), filtered and concentrated in vacuo. The crude alcohol 4 was purified by FCC (silica gel, 1:1, hexane/$CH_2Cl_2$).

EXAMPLE 5

1-Thiophen-2-yl-methylcyclobutanecarbaldehyde (5)

Oxalyl chloride (50 mL, 0.10 mmol) was added to $CH_2Cl_2$ (150 mL) at 23° C. and was cooled to −78° C. DMSO (16 g, 0.20 mmol) was added dropwise to the mixture and stirring was continued for 15 min. A solution of alcohol 4 (7.9 g, 0.041 mmol) in $CH_2Cl_2$ (50 mL) was then added dropwise, after which $Et_3N$ (44 g, 0.44 mmol) was added and the mixture was warmed to 23° C. After 1 h, the mixture was poured into saturated aqueous $NaHCO_3$ and the organic layer was separated. The aqueous layer was extracted with $CH_2Cl_2$ (2×) and the combined organic portions were washed with brine, dried ($Na_2SO_4$), concentrated in vacuo and purified by FCC (silica gel, hexane; 2:1, hexane/$CH_2Cl_2$) to afford the above named aldehyde 5.

EXAMPLE 6

1-(1-Thiophen-2-yl-methylcyclobutyl)but-2-yn-1-ol (6)

A solution of propylmagnesium bromide (360 mL of a 0.5M solution in THF, 0.180 mmol; 0.5 M in THF) was added dropwise to a solution of aldehyde 5 (7.0 g, 36 mmol) in THF (200 mL) while the mixture was maintained at ambient temperature. After having stirred 3 h at 23° C., the reaction was poured into saturated aqueous $NH_4Cl$ and extracted with $Et_2O$. The organic portion was separated and was washed with saturated aqueous $NaHCO_3$, brine, then dried ($Na_2SO_4$) and concentrated in vacuo. FCC (silica gel, hexane; 1:1, hexane/$CH_2Cl_2$) gave 6.2 g of the above named alkyne 6.

EXAMPLE 7

1-(1-Thiophen-2-yl-methylcyclobutyl)but-3-yn-1-ol (7)

A dry round bottom flask was charged with potassium hydride (5.5 g, 48 mmol; 35% by wt dispersion in oil) and the oil was removed by hexane rinse (3×). Aminopropylamide (39 mL) was added to the mixture and it was stirred until effervescence ceased. The mixture was then cooled to 0° C. and the alkyne 6 (2 g, 9.1 mmol) was added and the reaction stirred at 23° C. for 1 h. The reaction was quenched with MeOH (2 mL) and water. The mixture was extracted with $Et_2O$ (3×) and the combined organic layer was washed with 1N HCl, brine, dried ($Na_2SO_4$) and concentrated in vacuo. FCC (silica gel, 1:1 hexane/$CH_2Cl_2$) gave 570 mg of the above named alkyne 7.

EXAMPLE 8 tert-Butyldimethyl[1-(1-thiophen-2-yl-methylcyclobutyl)but-3-ynyloxy]silane (8)

To a cooled (0° C.) solution of alkyne 7 (200 mg, 0.9 mmol), $CH_2Cl_2$ (5 mL) and triethylamine (275 mg, 2.72 mmol) was added tert-butyldimethylsilyl trifluoromethanesulfonate (360 mg, 1.36 mmol) dropwise. After having stirred for 5 min at 0° C., the mixture was warmed to 23° C. and stirred an additional hour. The reaction was then quenched with saturated aqueous $NaHCO_3$ and extracted with $CH_2Cl_2$ (2×). The combined organics were washed with 1N HCl, saturated aqueous $NaHCO_3$, brine then were dried ($Na_2SO_4$), filtered and concentrated in vacuo. FCC (silica gel, 100% hexane) gave 695 mg of the above named compound 8.

EXAMPLE 9 tert-Butyl-[(E)-4-iodo-1-(1-thiophen-2-ylmethylcyclobutyl)but-3-enyloxy]dimethylsilane (9)

$Cp_2ZrHCl$ (304 mg, 1.18 mmol) was added to a solution of alkyne 8 (263 mg, 0.786 mmol) in $CH_2Cl_2$ (5 mL) at 23° C. and stirring was maintained for 20 min. N-iodosuccinimide (247 mg, 1.18 mmol) was added to the mixture and stirring was continued for an additional 30 min. The mixture was concentrated in vacuo, diluted with hexane/$Et_2O$, filtered and concentrated in vacuo. FCC (silica gel, 100% hexane) gave 360 mg of the above named compound 9.

EXAMPLE 10

7-[(R)-3-(tert-Butyldimethylsilanyloxy)-5-oxo-cyclopent-1-enyl]heptanoic Acid Methyl Ester (10)

The named compound was purchased from Nissan Chemical Industries, LTD, Tokyo 101-0054 Japan.

EXAMPLE 11

7-{(1R,2R,3R)-2-[(E)-(tert-Butyldimethylsilanyloxy)-(1-thiophen-2-yl-methylcyclobutyl)but-1-enyl]-3-[(dimethylethyl)dimethylsilanyloxy]-5-oxo-cyclopentyl}heptanoic Acid Methyl Ester (11)

To a solution of vinyl iodide 9 (120 mg, 0.259 mmol) in $Et_2O$ (1.5 mL) at −78° C. was added t-BuLi (0.35 mL of a 1.5M solution in THF, 0.52 mmol). After the mixture had stirred 30 min at −78° C., 2-thienyl(cyano)copper lithium (1.14 mL, 0.285 mmol) was added and stirring was continued for an additional 30 min. The reaction was then treated with a solution of the enone 10 (91.6 mg, 0.259 mmol) in $Et_2O$ (1 mL). After several minutes had passed, the reaction had solidified and 0.5 mL $Et_2O$ was added. The reaction was stirred 1 h at −78° C., was poured into saturated aqueous NH₄Cl and then was extracted with EtOAc (3×). The combined organic portions were washed with brine, filtered and concentrated in vacuo. FCC (silica gel, 100% hexane; 9:1, hexane/EtOAc) gave 63 mg of the above named compound 11.

EXAMPLE 12

7-{(1R,2R,3R)-3-Hydroxy-2-[(E)-4-hydroxy-4-(1-thiophen-2-yl-methylcyclobutyl)but-1-enyl]-5-oxo-cyclopentyl}heptanoic Acid Methyl Ester (12H)

7-{(1R,2R,3R)-3-Hydroxy-2-[(E)-4-hydroxy-4-(1-thiophen-2-yl-methylcyclobutyl)but-1-enyl]-5-oxo-cyclopentyl}heptanoic Acid Methyl Ester (12L)

Hydrogen fluoride-pyridine (0.091 mL) was added to a solution of the bis-TBS ether 11 (63 mg, 0.912 mmol) in $CH_3CN$ (3 mL) at 23° C. After having stirred for 3 h, the mixture was quenched with saturated aqueous $Na_2CO_3$ and extracted with EtOAc (3×). The combined organic portions were washed with 1N HCl, saturated aqueous $NaHCO_3$, brine, and were then dried ($Na_2SO_4$), filtered and concentrated in vacuo. FCC (silica gel, 3:2 hexane/EtOAc followed by 1:1, hexane/EtOAc) gave a higher $R_f$ diol (10 mg) and a lower $R_f$ diol (30 mg), hereinafter, designated as named compounds 12H and 12L, respectively).

EXAMPLE 13H

7-{(1R,2R,3R)-3-Hydroxy-2-[(E)-4-hydroxy-4-(1-thiophen-2-yl-methylcyclobutyl)but-1-enyl]-5-oxocyclopentyl}heptanoic Acid (13H)

Methyl ester 12H (4.8 mg, 10.4 mmol) and PLE (0.134 mmol, 45 mmol) were stirred in phosphate buffer (2 mL, pH 7.2) at 23° C. over 16 h. After the reaction was complete, the mixture was filtered and the aqueous phase was extracted with EtOAc (3×). The combined organic phases were washed with brine, dried ($Na_2SO_4$), filtered and concentrated in vacuo. FCC (silica gel, 1:1, hexane/EtOAc; EtOAc) gave of the above named acid 13H.

EXAMPLE 13L

7-{(1R,2R,3R)-3-Hydroxy-2-[(E)-4-hydroxy-4-(1-thiophen-2-yl-methylcyclobutyl)but-1-enyl]-5-oxo-cyclopentyl}heptanoic Acid (13L)

Methyl ester 12L was reacted according to Example 13H to yield the above named compound.

EXAMPLE 14

(Z)-7-[(R)-3-(tert-Butyldimethylsilanyloxy)-5-oxo-cyclopent-1-enyl]hept-5-enoic Acid Methyl Ester (14)

The named compound was purchased from Nissan Chemical Industries, LTD, Tokyo 101-0054 Japan.

EXAMPLE 15

(Z)-7-{(1R,2R,3R)-2-[(E)-(tert-Butyldimethylsilanyloxy)-(1-thiophen-2-yl-methylcyclobutyl)but-1-enyl]-3-[(dimethylethyl)dimethylsilanyloxy]-5-oxo-cyclopentyl}hept-5-enoic Acid Methyl Ester (15)

The compound of Example 14, above, was reacted in accordance with the process of Example 11 to yield the above named compound.

EXAMPLE 16

(Z)-7-{(1R,2R,3R)-3-Hydroxy-2-[(E)-4-hydroxy-4-(1-thiophen-2-yl-methylcyclobutyl)but-1-enyl]-5-oxo-cyclopentyl}hept-5-enoic Acid Methyl Ester (16H)

(Z)-7-{(1R,2R,3R)-3-Hydroxy-2-[(E)-4-hydroxy-4-(1-thiophen-2-yl-methylcyclobutyl)but-1-enyl]-5-oxo-cyclopentyl}hept-5-enoic Acid Methyl Ester (16L)

The compound of Example 15 is reacted in accordance with the process of Example 12 to yield a higher $R_f$ diol (6.0 mg) and a lower $R_f$ diol (6.0 mg), hereinafter, designated as 16H and 16L, respectively.

EXAMPLE 17H (Z)-7-{(1R,2R,3R)-3-Hydroxy-2-[(E)-4-hydroxy4-(1-thiophen-2-yl-methylcyclobutyl)but-1-enyl]-5-oxo-cyclopentyl}hept-5-enoic Acid (17H)

The compound 16H of Example 16 is reacted in accordance with the process of Example 13H to yield the above named compound.

EXAMPLE 17L (Z)-7-{(1R,2R,3R)-3-Hydroxy-2-[(E)-4-hydroxy-4-(1-thiophen-2-yl-methylcyclobutyl)but-1-enyl]-5-oxo-cyclopentyl}hept-5-enoic Acid (17L)

The compound 16L of Example 16 is reacted in accordance with the process of Example 13H to yield the above named compound.

RADIOLIGAND BINDING

Recombinant $EP_2$ receptor; transient transfectants COS-7 cells were transiently transfected using Lipofectin (Gibco-BRL life Technologies, Gaitherburg, Md., U.S.A.) according to manufacturer's protocols. For binding studies, $2 \times 10^6$ cells were plated onto 150 mm dishes 24 h prior to transfection. Each plate was transfected with 50 μg plasmid DNA and 50 μL lipofectin. Cells were collected and membranes prepared at 48 h post-transfection, and frozen at −80° C. until use.

Plasma membrane preparations were thawed at room temperature and used at a final 1 mg/mL concentration in a 500 μL volume. The binding of [$^3$H]-$PGE_2$ (specific activity 180 Ci mmol$^{-1}$) were determined in duplicate and experiments were replicated three times. Incubations were for 60 min at 25° C. and were terminated by the addition of 4 mL of ice-cold 50 μM TRIS-HCl, followed by rapid filtration through Whatman GF/B filters and three additional 4 mL washes in a cell harvester (Brandel). Competition studies were performed using a final concentration of 5 nM [$^3$H]-$PGE_2$ and non-specific binding determined with 10 μM of the respective unlabelled prostanoid.

Certain of the above compounds were tested for activity in the recombinant human $EP_2$ receptor assay described above and the results are reported in Table 1, below.

| Structure | hEP$_2$ |
|---|---|
|  12H | >10$^4$ |
| 12L | >10$^4$ |
| 13H | >200 |
| 13L | >300 |
| 16H | >10$^4$ |
| 16L | 3400 |

-continued

| Structure | hEP$_2$ |
|---|---|
|  17H | 1500 |
| 17L | 74 |

EP$_2$ activity indicates that the compounds of this invention are useful in treating asthma, dysmenorrhea as well as glaucoma and lowering intraocular pressure.

Other potential therapeutic applications are in osteoporosis, constipation, renal disorders, sexual dysfunction, baldness, diabetes, cancer and in disorder of immune regulation.

The compounds of the invention may also be useful in the treatment of various pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by oral, transdermal, parenteral, subcutaneous, intravenous, intramuscular, intraperitoneal, transdermal, or buccal routes.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tables or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension which comprises administering to a mammal having ocular hypertension a therapeutically effective amount of a compound represented by formula I:

wherein the hatched segment represents an α bond, the solid triangle represents a β bond, the wavy segment represents α or β bond, dashed lines represent a double bond or a single bond, $R^3$ is heteroaryl or a substituted heteroaryl radical, $R^1$ and $R^2$ are independently selected from the group consisting of hydrogen or a lower alkyl radical having up to six carbon atoms, or a lower acyl radical having up to six carbon atoms, R is selected from the group consisting of $CO_2R^4$, $CONR^4_2$, $CH_2OR^4$, $CONR^4SO_2R^4$, $P(O)(OR^4)$ and wherein $R^4$ is selected from the group consisting of H, phenyl and lower alkyl having from one to six carbon atoms and n is 0 or an integer of from 1 to 4.

2. The method of claim 1 wherein the substituent on the heteroaryl radical is selected from the group consisting of $C_1$ to $C_6$ alkyl; $OR^4$; $CO_2R^4$; halogen, trifluoromethyl; $COR^4$; $COCF_3$; $SO_2NR^4$, $NO_2$; and CN.

3. The method of claim 2 wherein said compound is represented by formula II:

wherein Z is selected from the group consisting of O and S, A is selected from the group consisting of N, —CH, and C, $R^5$ is selected from the group consisting of hydrogen, halogen, lower alkyl having from 1 to 6 carbon atoms, and lower alkoxy having from 1 to 6 carbon atoms, $R^6$ and $R^7$ are selected from the group consisting of hydrogen, halogen, lower alkyl having from 1 to 6 carbon atoms, lower alkoxy having from 1 to 6 carbon atoms or, together with

$R^6$ and $R^7$ forms a condensed aryl ring.

4. The method of claim 3 wherein said compound is represented by formula III:

5. The method of claim 4 wherein the dashed line represents a double bond.
6. The method of claim 4 wherein the dashed line represents a single bond.
7. The method of claim 5 wherein R is $CO_2R^4$ and $R^4$ is H.
8. The method of claim 6 wherein R is $CO_2R^4$ and $R^4$ is H.
9. The method of claim 5 wherein R is $CO_2R^4$ and $R^4$ is methyl.
10. The method of claim 6 wherein R is $CO_2R^4$ and $R^4$ is methyl.
11. The method of claim 4 wherein R is $CO_2R^4$.
12. The method of claim 11 wherein $R^4$ is selected from the group consisting of H and lower alkyl.
13. The method of claim 4 wherein A is $C_2$ nd $R_5$, $R_6$ and $R_7$ are H.
14. The method of claim 13 wherein said compound is 7-{(1R,2R,3R)-3-Hydroxy-2-[(E)-4-hydroxy-4-(1-thiophen-2-ylmethylcyclobutyl)but-1-enyl]-5-oxo-cyclopentyl}heptanoic acid methyl ester.
15. The method of claim 13 wherein said compound is 7-{(1R,2R,3R)-3-Hydroxy-2-[(E)-4-hydroxy-4-(1-thiophen-2-ylmethylcyclobutyl)but-1-enyl]-5-oxocyclopentyl}heptanoic acid.
16. The method of claim 13 wherein said compound (Z)-7-{(1R,2R,3R)-3-Hydroxy-2-[(E)-4-hydroxy-4-(1-thiophen-2-ylmethylcyclobutyl)but-1-enyl]-5-oxo-cyclopentyl}hept-5-enoic acid methyl ester.
17. The method of claim 13 wherein said compound is (Z)-7-{(1R,2R,3R)-3-Hydroxy-2-[(E)-4-hydroxy-4-(1-thiophen-2-ylmethylcyclobutyl)but-1-enyl]-5-oxo-cyclopentyl}hept-5-enoic acid.
18. An ophthalmic solution comprising a therapeutically effective amount of a compound of formula I, as defined in claim 1, or a pharmaceutically acceptable salt thereof, in admixture with a non-toxic, ophthalmically acceptable liquid vehicle, packaged in a container suitable for metered application.
19. The ophthalmic solution of claim 18 wherein said compound is a compound of Formula III.
20. A pharmaceutical product, comprising a container adapted to dispense the contents of said container in metered form; and an ophthalmic solution in said container comprising a compound of formula I as defined in claim 1, or a pharmaceutically acceptable salt thereof, in admixture with a non-toxic, ophthalmically acceptable liquid vehicle.
21. The product of claim 20 wherein said compound is a compound of Formula III.

22. The compound represented by formula I:

wherein the hatched segment represents an α bond, the solid triangle represents a β bond, the wavy segment represents an α or β bond, dashed lines represent a double bond or a single bond, $R^3$ is heteroaryl or a substituted heteroaryl radical, $R^1$ and $R^2$ are independently selected from the group consisting of hydrogen or a lower alkyl radical having up to six carbon atoms, or a lower acyl radical having up to six carbon atoms, R is selected from the group consisting of $CO_2R^4$, $CONR^4_2$, $CH_2OR^4$, $CONR^4SO_2R^4$, $P(O)(OR^4)$ and wherein $R^4$ is selected from the group consisting of H, phenyl and lower alkyl having from one to six carbon atoms and n is 0 or an integer of from 1 to 4.
23. The compound of claim 22 wherein R is $CO_2R^4$.
24. The compound of claim 23 wherein $R^4$ is selected from the group consisting of H and lower alkyl.
25. The compound of claim 24 wherein said compound is represented by the formula 26. The compound of claim 25 wherein A is C and $R_5$, $R_6$ and $R_7$ are H.
27. The compound of claim 26 wherein said compound is selected from the group consisting of
7-{(1R,2R,3R)-3-Hydroxy-2-[(E)-4-hydroxy-4-(1-thiophen-2-yl-methylcyclobutyl)but-1-enyl]-5-oxo-cyclopentyl}heptanoic acid methyl ester
7-{(1R,2R,3R)-3-Hydroxy-2-[(E)-4-hydroxy-4-(1-thiophen-2-yl-methylcyclobutyl)but-1-enyl]-5-oxocyclopentyl}heptanoic acid
(Z)-7-{(1R,2R,3R)-3-Hydroxy-2-[(E)-4-hydroxy-4-(1-thiophen-2-yl-methylcyclobutyl)but-1-enyl]-5-oxo-cyclopentyl}hept-5-enoic acid methyl ester
(Z)-7-{(1R,2R,3R)-3-Hydroxy-2-[(E)-4-hydroxy-4-(1-thiophen-2-yl-methylcyclobutyl)but-1-enyl]-5-oxo-cyclopentyl}hept-5-enoic acid.

* * * * *

UNITED STATES PATENT AND TRADEMARK OFFICE
CERTIFICATE OF CORRECTION

PATENT NO. : 6,376,533 B1
DATED : April 23, 2002
INVENTOR(S) : Burk et al.

It is certified that error appears in the above-identified patent and that said Letters Patent is hereby corrected as shown below:

<u>Column 2,</u>
Line 14, delete "(PGEI)" and insert in place thereof -- (PGE1) --

<u>Column 10,</u>
Line 22, delete "hydroxy4" and insert in place thereof -- hydroxy-4 --

Signed and Sealed this

Twenty-fifth Day of June, 2002

*Attest:*

*Attesting Officer*

JAMES E. ROGAN
*Director of the United States Patent and Trademark Office*